United States Patent
Semenza et al.

(10) Patent No.: US 9,657,314 B2
(45) Date of Patent: May 23, 2017

(54) ANTIMICROBIAL METHOD FOR FERMENTATION PROCESSES

(75) Inventors: Reed Semenza, Galt, CA (US); Michael Welker, Okauchee, WI (US)

(73) Assignee: DELAVAL HOLDING AB, Tumba (SE)

(*) Notice: Subject to any disclaimer, the term of this patent is extended or adjusted under 35 U.S.C. 154(b) by 0 days.

(21) Appl. No.: 13/817,955

(22) PCT Filed: Aug. 24, 2011

(86) PCT No.: PCT/US2011/048962
§ 371 (c)(1),
(2), (4) Date: Apr. 12, 2013

(87) PCT Pub. No.: WO2012/027469
PCT Pub. Date: Mar. 1, 2012

(65) Prior Publication Data
US 2013/0224814 A1    Aug. 29, 2013

Related U.S. Application Data

(60) Provisional application No. 61/493,880, filed on Jun. 6, 2011, provisional application No. 61/484,451, filed on May 10, 2011, provisional application No. 61/376,647, filed on Aug. 24, 2010.

(51) Int. Cl.
| | |
|---|---|
| *C12P 7/06* | (2006.01) |
| *C12M 1/00* | (2006.01) |
| *A01N 37/16* | (2006.01) |
| *A01N 59/00* | (2006.01) |

(52) U.S. Cl.
CPC ............ *C12P 7/06* (2013.01); *A01N 37/16* (2013.01); *C12M 21/12* (2013.01); *C12M 29/26* (2013.01); *C12M 45/06* (2013.01); *C12M 45/20* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 5,683,724 A | 11/1997 | Hei et al. | |
| 2008/0194518 A1* | 8/2008 | Mookerjee et al. | 514/55 |
| 2009/0061490 A1 | 3/2009 | Edwards et al. | |
| 2009/0233340 A1* | 9/2009 | Dailey et al. | 435/161 |
| 2009/0240088 A1 | 9/2009 | Fenton et al. | |
| 2010/0075006 A1 | 3/2010 | Semenza | |
| 2010/0261243 A1* | 10/2010 | Kloos | 435/161 |
| 2011/0230394 A1* | 9/2011 | Wiatr et al. | 514/2.4 |

FOREIGN PATENT DOCUMENTS

| | | | |
|---|---|---|---|
| CA | 2300807 A1 * | 9/2000 | |
| WO | WO 2009010836 A2 * | 1/2009 | |

OTHER PUBLICATIONS

Hilgren J et al. Inactivation of Bacillus anthracis spores by liquid biocides in the presence of food residue. 2007. Applied and Environmental Microbiology. vol. 73, No. 20. p. 6370-6377.*
Meneghin, S.P. et al, 'Chlorine dioxide against bacteria and yeasts from the alcoholic fermentation', Brazilian Journal of Microbiology, 2008, vol. 39, pp. 337-343.
Semenza, R., 'Controlling Bacteria During Corn Mash Fermentation: Oxiders can replace antibiotics in fermentation, boosting ethanol yields', Ethanol producer magazine, Jun. 10, 2011, URL: http://www.ethanolproducer.com/articles/7857/controlling-bacteria-during-corn-mash-fermentation.
International Search Report and Written Opinion for PCT/US2011/048962, dated Mar. 22, 2012, 13 pages.
Baldry M. G.: "The bactericidal, fungicidal and sporicidal properties of hydrogen peroxide and peracetic acid," Journal of applied bacteriology, Jun. 1983, pp. 417-423, vol. 54, No. 3, Blackwell Publishing Ltd., Oxford, GB.
The Supplemental Partial European Search Report dated Jul. 13, 2016, in EP 11820592 filed Mar. 4, 2013.

* cited by examiner

*Primary Examiner* — Paul Holland
(74) *Attorney, Agent, or Firm* — Hovey Williams LLP

(57) ABSTRACT

A system and method for controlling bacteria, especially lactic and acetic acid bacteria in the production of ethanol using an organic oxidizing compound in combination with an inorganic oxidizer is provided. Particularly, a mixture of one or more peroxy acids and one or more peroxide compounds is introduced into a fermentation mash so as to inhibit or reduce levels of bacteria that compete with yeast for the fermentation sugars. The peroxy acid and peroxide compounds largely are consumed during the fermentation process and are generally not present in the fermentation by-products, especially recovered distiller's grains.

16 Claims, 2 Drawing Sheets

ANTIMICROBIAL METHOD FOR FERMENTATION PROCESSES

RELATED APPLICATIONS

This application claims the benefit of U.S. Provisional Patent Application No. 61/376,647, filed Aug. 24, 2010; U.S. Provisional Patent Application No. 61/484,451, filed May 10, 2011; and U.S. Provisional Patent Application No. 61/493,880, filed Jun. 6, 2011, all of which are incorporated by reference herein in their entireties.

BACKGROUND OF THE INVENTION

Field of the Invention

The present invention relates generally to antimicrobial compositions and processes for using those compositions in fermentation processes. More specifically, the invention relates to the use of organic oxidizing compounds as an alternative to antibiotic agents to control bacteria in the fermentation mash of an ethanol production system.

Description of the Related Art

In ethanol production, yeast (*Saccaromyces cerevisiae*) is used to convert sugar into ethanol. Other microorganisms can compete with the yeast for the sugars. These microorganisms include, but are not limited to, lactic acid and acetic acid bacteria. When acid bacteria grow, they compete with the supply of sugar resulting in less sugar for ethanol production. Also, acid forming bacteria can create low pH conditions that tend to inhibit the growth of the ethanol producing yeast.

In order to control the growth of acid producing bacteria, antibiotics are added to the fermentation tanks. The antibiotics allow the yeast to kill much of the acid bacteria, but the antibiotics do not harm the yeast. The conventional method calls for the addition of 3 to 5 pounds of antibiotic, usually Virginiamycin, per 500,000 gallons of corn mash in the fermenter. The actual dose of antibiotics is determined by the level of lactic acid in the corn mash during the first 30 hours of fermentation.

Antibiotics, though generally effective, have several major disadvantages. The main disadvantage is that the antibiotics carry through the fermentation process and distillation process and end up in the distillers grains (DGs). DGs are composed of protein, oil and fiber and are what is left of the corn mash after fermentation. The DGs provide a valuable feed product but with trace antibiotics, many cattle feeders are reluctant to use DGs or must ration the DGs in the animal feed. Trace antibiotics in the DGs are thought to cause bacteria to mutate to an antibiotic resistant strain. The FDA is currently considering banning the use of antibiotics in ethanol production due to the carry over of trace amounts of antibiotics. A second disadvantage of antibiotics is that acid bacteria can become resistant over time rendering the use of antibiotics less effective and resulting in ethanol production losses.

SUMMARY OF THE INVENTION

According to one embodiment of the present invention there is provided a method for reducing microbial levels within a fermentation system. The method comprises introducing an organic oxidizing compound and an inorganic oxidizing compound into a fermentation mash located within the system.

In another embodiment according to the present invention there is provided a method for reducing microbial levels within an ethanol fermentation system. The method comprises introducing a quantity of peracetic acid and a quantity of hydrogen peroxide into a corn mash located within the system. In particular embodiments, the method is performed without the introduction of antibiotic compounds into the corn mash. Even more particularly, the peracetic acid is introduced into the corn mash at a level of between about 5 to about 30 ppm.

In still another embodiment according to the present invention there is provided an ethanol fermentation system. The system comprises at least one fermentation mash cooler, a fermentation tank located downstream from the cooler, and at least one injection station adapted to deliver a quantity of an organic oxidizing compound and an inorganic oxidizing compound into a fermentation mash located within the system.

DETAILED DESCRIPTION OF THE PREFERRED EMBODIMENT

Figure 1:
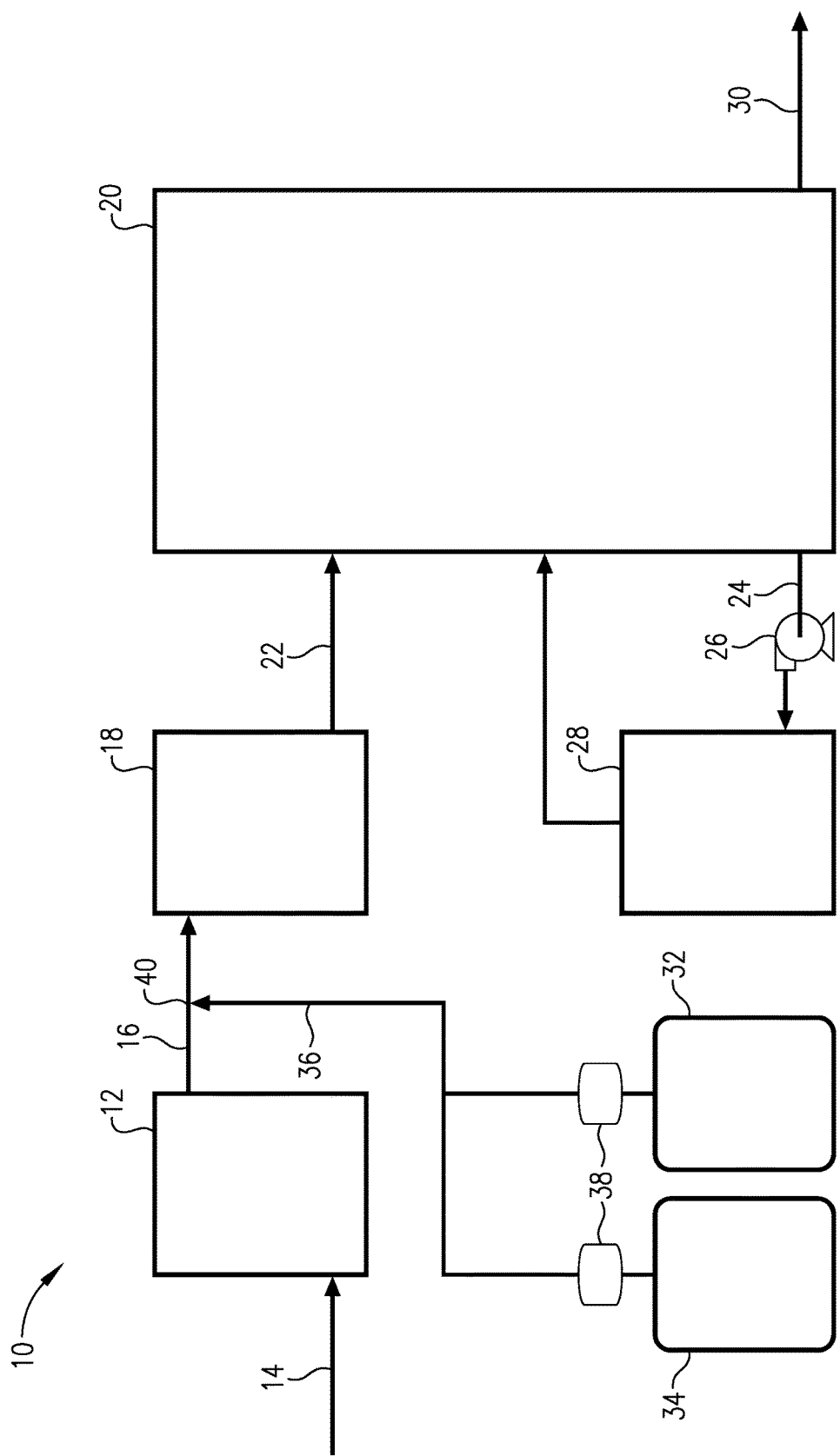
FIG. 1 is a schematic diagram of an exemplary fermentation system according to the present invention employing an apparatus for delivering organic oxidizing compound and peroxide compound.

As discussed previously, the presence of certain types of bacteria in a fermentation system can compete with the fermentation yeast for sugars thereby reducing the yield of the system. The present invention, in certain embodiments, utilizes an antimicrobial system that advantageously is decomposed by the fermentation operation so that is does not carry through into the fermentation by-products, especially the distillers grains, unlike conventional antibiotic treatments.

According to one embodiment of the present invention, an organic oxidizing compound and an inorganic oxidizing compound are introduced into a fermentation mash located within a fermentation system. In particular embodiments, the organic oxidizing compound comprises one or more peroxy acids, such as an organic C1 to C18 peroxy acid. Exemplary peroxy acids include peracetic acid (PAA) or peroctanoic acid. In other embodiments, a germicidal fatty acid such as octanoic acid, nonanoic acid, or decanoic acid may be used in conjunction with the organic oxidizing compound. The organic oxidizing compound may react with a portion of the germicidal fatty acid to form the peroxy acid form thereof (i.e., peroctanoic acid, pernonanoic acid, and perdecanoic acid). The germicidal fatty acid can help contribute to enhanced germicidal efficacy of the overall process. However, caution should be exercised to avoid use of germicidal fatty acids at levels that might harm the yeast present in the fermentation mash. In still other embodiments, the organic oxidizing compound can be a mixture of more than one organic oxidizing compound, such as a mixture of peracetic acid and octanoic acid.

Peracetic acid naturally exists in equilibrium with acetic acid and hydrogen peroxide as illustrated below and is commercially available in solution with acetic acid and hydrogen peroxide in order to maintain stability.

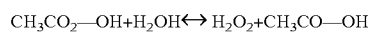

Exemplary peracetic acid solutions include Proxitane®, available from Solvay Chemicals, Inc., Delasan MP®, available from DeLaval Cleaning Solutions, and Tsunami®, available from Ecolab.

| Product | Supplier | % PAA | % H$_2$O$_2$ | % Acetic Acid | Other |
|---|---|---|---|---|---|
| Peracetic Acid 5% | FMC | 5% | 22% | 10% | |
| Peracetic Acid 15% | FMC | 15% | 10% | 36% | |
| Delasan MP | DeLaval | 15% | 6% | 30-40% | |
| Proxitane | Solvay | 5% | 22% | NA | |
| Matrix | Ecolab | 3-7% | 5-10% | 15-40% | 3-7 peroctanoic; 1-5 caprylic acid |
| Premium Peroxide II | West Agro, Inc. | 5.6% | 26.5% | NA | |

NA = information not available
Information taken from commercial literature or MSDS In some fermentation systems, the demand for the organic oxidizing compound can be quite high, thereby requiring increased amounts of the organic oxidizing compound to be added to the system in order to achieve the desired antimicrobial effect. This increased demand for the organic oxidizing compound can be tied to, among other things, the level of certain organic or biological materials present in the fermentation mash. Further, because in certain embodiments the organic oxidizing compound is acidic, simply increasing the amount of the organic oxidizing compound to satisfy the oxidative demand may decrease the pH of the fermentation mash and adversely affect ethanol production. In order to reduce the demand for the organic oxidizing compound, without simply introducing higher levels of organic oxidizing compound into the fermentation mash, one or more inorganic oxidizing compounds can be introduced into the system. In particular embodiments, the inorganic oxidizing compound is a peroxide compound, and more particularly, hydrogen peroxide is selected as the peroxide compound due to its availability and relatively low cost as compared with the organic oxidizing compound. Alternative inorganic oxidizing compounds include sodium percarbonate, sodium perborate, and peroxymonosulfate.

In certain embodiments of the present invention, to maximize flexibility in controlling bacteria in the fermentation process, it is advantageous to be able to independently control the levels of the organic oxidizing compound (such as peracetic acid) and inorganic oxidizing compound (such as hydrogen peroxide) added to the fermentation mash. For example, peracetic acid is supplied commercially as an equilibrium mixture of peracetic acid, acetic acid, and hydrogen peroxide. Therefore, in certain embodiments, it may be advantageous to use a peracetic acid source that has a minimal amount of hydrogen peroxide relative to the concentration of peracetic acid. However, in other embodiments the organic oxidizing compound and inorganic oxidizing compound may be supplied together in a premixed form, and then the premix introduced into the fermentation mash. Certain premix formulations comprise the organic oxidizing compound at a level of between about 5% to about 30% by weight, or between about 10% to about 25% by weight, or about 15% by weight, and the inorganic oxidizing compound at a level of between about 15% to about 55% by weight, or between about 25% to about 50% by weight, or about 45% by weight.

The fermentation system utilizes a fermentation mash as the source of sugars for the yeast that are responsible for alcohol production. The fermentation mash is generally an aqueous suspension of plant-based materials, especially those derived from corn, wheat, sugar beets, sugar cane, molasses, potatoes, millet, and switchgrass. Additionally, other cellulosic materials or biomass, such as wood or straw, may be used to create the fermentation mash. In certain embodiments, these cellulosic materials may need to undergo pretreatment and cellulose hydrolysis in order to render them suitable for use in a fermentation process. Typically, the mash is made by mixing the plant-based material with heated, often boiling, water. The hot mash is cooled before being sent to a fermentation vessel where yeast is added and fermentation is carried out. Control of bacteria, such as lactic acid bacteria, is especially important between formation of the fermentation mash and the fermentation stage. Thus, in certain embodiments according to the present invention, the organic oxidizing compound and peroxide compound are introduced into the fermentation system at some point between the cooling of the mash and the beginning of fermentation.

It has been discovered that to achieve sufficient antimicrobial efficacy, the organic oxidizing compound need only be added to the fermentation mash at a level of less than 50 ppm. In certain embodiments, the organic oxidizing compound is added to the fermentation mash at a level of between about 5 to about 30 ppm, or even at a level of between about 10 to about 25 ppm. Likewise, the peroxide compound need only be introduced into the fermentation mash at a level of less than 50 ppm. In particular embodiments, the peroxide compound is added to the fermentation mash at a level of between about 5 to about 30 ppm, or even at a level of between about 10 to about 25 ppm. In still further embodiments, the organic oxidizing compound and peroxide compound are introduced into the fermentation system in substantially equal proportions. It is noted that the peroxide concentration levels noted represent the combined concentration of peroxide included with the organic oxidizing compound, such as peracetic acid, and the peroxide that is added independently. In yet other embodiments, the organic oxidizing compound and peroxide compound are introduced into the fermentation system in sufficient quantities so that lactic acid levels within the liquid portion of the fermentation system do not exceed about 0.2%, 0.1% or 0.01% by weight. Historical records indicate that without any antimicrobial system being used, lactic acid levels within the fermentation system rise to above 1.0%.

The peroxide and organic oxidizing compound may be added simultaneously at the same point in the process or a portion of the peroxide may be added prior to addition of the organic oxidizing compound. Where a portion of peroxide is added upstream of the organic oxidizing compound, it will likely consume more of the oxidative demand and reduce the amount of organic oxidizing compound required.

In certain embodiments, the organic oxidizing compound and peroxide compound are consumed during the course of the fermentation process so that little or none of these compounds can be found in the distiller's grains recovered from the fermentation vessel. In such embodiments, the organic oxidizing compound and peroxide compound decompose into environmentally friendly by-products. Further, such by-products do not pose a threat to use of the distiller's grains as animal feed. While embodiments of the invention can be carried out using any desired levels of the organic oxidizing compound or peroxide compound, in certain applications caution should be exercised so as to avoid using levels of these compounds that will not completely decompose and having these compounds be present in the distiller's grains. In certain embodiments, the distiller's grains recovered from the fermentation process comprise less than 1 ppm, or less than 0.1 ppm, or even less than 0.05 ppm of the organic oxidizing compound. Note, the oxidizing compounds were found to be non-detectable in the distillers grains at a detection limit of 0.05 ppm.

The use of the organic oxidizing compound and peroxide compound to control undesirable bacteria in the fermentation system also permits the fermentation process to be carried out without the use of antibiotics, such as Virginiamycin. Thus, the distiller's grains produced by the fermentation system will be substantially free of antibiotics.

FIG. 1 illustrates an exemplary fermentation system 10 made in accordance with one embodiment of the present invention. The illustrated system is described as a corn mash fermentation system employing peracetic acid and hydrogen peroxide as the antimicrobial compounds. However, one of ordinary skill in the art can appreciate that this description is merely illustrative of the general principles of the present invention and that other fermentation systems, organic oxidizing compounds, and peroxides can be substituted for the exemplary materials.

System 10 includes a corn mash primary cooler 12 which cools incoming corn mash stream 14 from a temperature of 180° F. to 140° F. The cooled corn mash 16 is then directed to a secondary cooler 18 where the temperature is lowered to near ambient conditions (approximately 90° F.). Once the temperature of the corn mash has been sufficiently lowered, it is directed to fermentation tank 20 via stream 22 where yeast is added and the fermentation of sugars contained in the corn mash is carried out. A recycle stream 24 is withdrawn from fermentation tank 20 by a fermenter recycle pump 26 and passed through a fermenter cooler 28 so that the temperature within fermentation tank 20 can be controlled. After fermentation has sufficiently progressed, the corn mash, now containing approximately 14% ethanol, is withdrawn from fermentation tank 20 via stream 30. The fermented mixture is then sent to separation apparatus (not shown), such as a centrifuge, whereby the liquids are separated from the solids. The liquids are then delivered to one or more distillation columns (not shown) for separation of ethanol, and the solids are recovered as distiller's grains.

In the embodiment illustrated, peracetic acid and hydrogen peroxide are pumped from respective reservoirs 32, 34, such as plastic totes, into a common chemical transfer pipe 36 by electronic diaphragm pumps 38. The combined peracetic acid and hydrogen peroxide stream is introduced into a corn mash transfer header 40 where the peracetic acid mixture is dissolved into the corn mash due to the high corn mash flow rate. Introduction of the corn mash into secondary cooler 18 creates the turbulence necessary for rapid distribution of the peracetic acid and hydrogen peroxide throughout the corn mash. Thus, by the time the acid treated corn mash reaches the fermentation tank 20, the acid will have been thoroughly mixed, enabling it to work as an antimicrobial in a uniform manner.

It is noted that the peracetic acid and hydrogen peroxide can be introduced into the corn mash at some other location, such as after secondary cooler 18 or directly into fermentation tank 20. Alternatively, the peracetic acid and hydrogen peroxide can be added through independent chemical transfer pipes as opposed to a common pipe. Also, any system for introducing the peracetic acid and hydrogen peroxide into the corn mash can be used as the fermentation process operator deems fit.

In addition to the benefits of maintaining high ethanol recovery levels without the use of conventional antibiotics that would be carried through into the distiller's grains, certain embodiments of the present invention prevent biofouling of wetted surfaces downstream from the organic oxidizing compound and peroxide injection point. This feature increases the length of time that the fermentation equipment can remain in service without required cleaning thereby increasing the overall efficiency of the fermentation system.

EXAMPLE

A number of full scale trials were conducted in order to evaluate the efficacy of introducing peracetic acid and hydrogen peroxide into a fermentation system was evaluated and compared to the use of conventional antibiotics. The ethanol plant tested is a 20 MGPY plant having a modified Delta T design. The plant process flow is as follows:

Corn mash cooler stage one→Corn mash cooler stage 2→fermenter F←→fermenter cooler→distillation The corn mash enters the stage one cooler at 180° F. and is cooled to 140° F. It then enters the stage 2 cooler and is cooled to 90° F. Flow through the cooler is 110 gpm. From the stage 2 cooler the mash is sent to the fermenter. Once in the fermenter, the corn mash is re-circulated through a plate and frame mash cooler. When the fermenter has been filled for 30 minutes, yeast is added to the recirculating corn mash. The fermenter takes about 23 hours to fill. Once filled, fermentation begins to accelerate releasing heat which is dissipated in the fermenter cooler. The fermenter mash is sent to distillation about 56 hours after the fermenter is filled. System parameters are as follows:

| Vessel | Volume (gal) | Recirc rate (gpm) | pH range | Temp (in/out) |
| --- | --- | --- | --- | --- |
| Mash cooler | 700 | 110 | 5.5-6.5 | 180° F./90° F. |
| Fermenter | 185,000 | 400 | 4-5.5 | 95° F./90° F. |

During fermentation, carbohydrates, ethanol, and organic acids are monitored in order to insure that the fermentation process is occurring normally and to insure that undesirable bacteria are kept under control. Also, the mash temperature is kept in a range of 90° F. to 95° F. Typical end fermenter process parameters are:

| Ethanol | Lactic acid | Acetic acid | pH | Cell count | Viable count (%) |
| --- | --- | --- | --- | --- | --- |
| 15.0 | 0.30 | 0.05 | 4.6 | 250 | 97 | pH: pH starts at 6.0 then slowly drops to 4.2 after 18 hours. Toward the end of fermentation, pH rises to 4.6.
Lactic acid: Lactic acid percent starts at 0.1 and stays mostly below 0.4% when lactic acid bacteria are under control When lactic acid bacteria are present in larger numbers, the lactic acid % can rise to as high as 0.8%.
Acetic acid: Acetic acid generally starts in a range of 0.03 to 0.05 and rises to 0.1. A rise above 0.15% results in reduced final ethanol and indicates that bacteria counts are out of control.

Test Procedure

A peracetic acid solution comprising 15% peracetic acid and 6% hydrogen peroxide, (PAA solution) and 31% hydrogen peroxide (HP) were added at a rate of 0.8 and 1 gallon per hour respectively to a stainless steel pipe that carried the mixture to a header located between the $1^{st}$ and $2^{nd}$ stage mash cooler. At the point of injection, the mash temperature was 140° F. and the mash flow rate was 110 gpm. The pumps used to pump both the HP and PAA solution were Prominent diaphragm pumps fitted with Teflon liquid ends. The dose of the PAA solution was 15 ppm (as PAA) and the dose of the HP was 40 ppm (as peroxide). However, the PAA solution and HP were fed for only 15 hours of the 23 hour fermentor fill time making the overall dose 9.8 ppm of PAA solution and 26 ppm of HP.

Samples were taken every hour at the mash cooler exit and fermentation tank. The samples were tested using a Hach DPD total chlorine test. Three (3) ml of sample was added to a test tube, then one DPD powder pillow was added to the sample. The sample was then stirred gently for 5 seconds and a pink color was observed at the bottom of the test tube. Peracetic acid (PAA) concentration was estimated based on the hue of pink color after 30 seconds. Hydrogen peroxide (HP) concentration was estimated after 6 minutes.

Normal corn mash tests on carbohydrates, ethanol, and organic acids were taken by plant personnel every 6 hours. Results were compared with normal historical averages when antibiotics were used. The testing with PAA and HP was conducted over a six-month period. Occasionally during this period, antibiotics (i.e., Virginiamycin at a level of 0.5-1 pound/200,000 gal corn mash) were used simultaneously with the PAA and HP for approximately 3 to 6 day stretches to determine what affect this might have on the performance of the system.

Test Results:

Mash cooler: PAA concentrations consistently measured at 3 to 4 ppm. Hydrogen peroxide was always positive with an estimated concentration of 10 to 15 ppm.

Fermenter corn mash: The corn mash was positive for PAA up to two hours into filling. After two hours, PAA was not detectable. HP was not detectable after 3 hours.

Organic acids: Both lactic and acetic acids stayed within normal ranges. Lactic acid generally ranged from 0.2% to 0.5%. Acetic acid generally ranged from 0.05% to 0.12%. When both PAA solution and antibiotics were used, lactic acid and especially acetic acid levels were lower than when only antibiotics were used. This indicated that the PAA/HP treatment was particularly effective in control of lactic and acetic acid bacteria. In fact, it appeared that under these circumstances, the yeast may have been using lactic and acetic acid as a food source.

Figure 2:
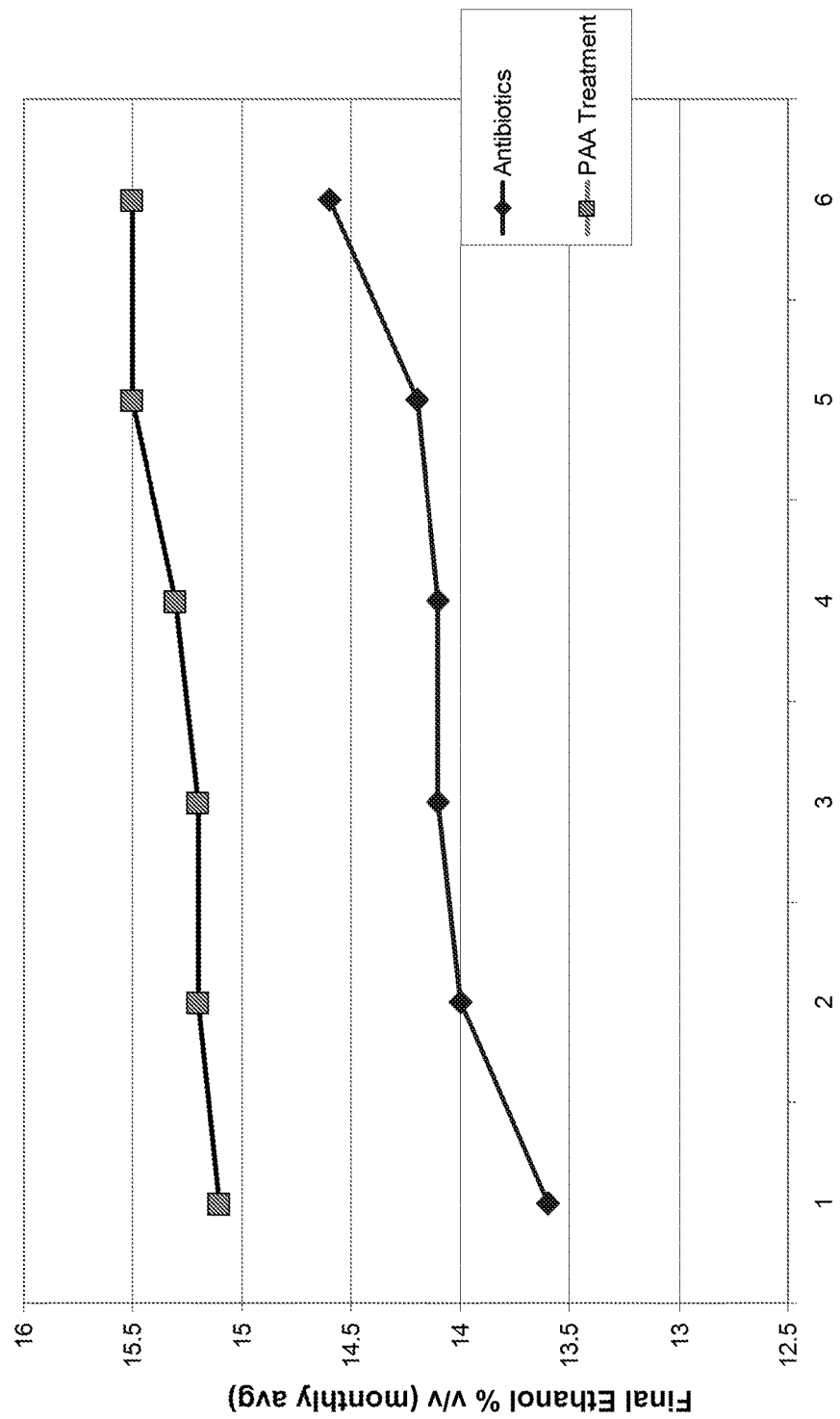
FIG. 2 is a chart depicting ethanol production levels for a commercial-scale trial in which peracetic acid and hydrogen peroxide were used in place of conventional antibiotics to control certain bacteria in the fermentation mash.

Alcohol production: As shown in FIG. 2, alcohol production for the six-month period in which the PAA/HP treatment was employed was approximately 8.5% higher than the previous six-month period when only antibiotics were used, even when organic acids did not decrease from normal. This result was not expected as alcohol production is thought to be inversely correlated with organic acids. Higher organic acid concentration usually results in lower ethanol concentration. It is likely that the removal of biofilms on transfer, heat exchanger, and tank surfaces resulted in decreased glucose losses and that the extra glucose was converted into ethanol. The tests indicated that the peracetic acid/hydrogen peroxide treatment program can effectively replace the use of antibiotics in preventing ethanol loss due to the formation of organic acids. No negative effects of the program were noted based on the balance of carbohydrates, ethanol, and organic acids taken in the number 1, 2 and 3 fermenters. Also, yeast cell counts and viability tests were all in the normal range.

Glycerol levels: It was observed that during those periods during which antibiotics were used with the PAA/HP treatment, glycerol levels tended to increase. When the antibiotics were removed, the glycerol levels tended to decrease. The increase in glycerol levels were indicative of the stress which the antibiotics placed on the yeast.

We claim:

1. A method for reducing bacteria levels within an ethanol fermentation system comprising:
    introducing a quantity of peracetic acid and a quantity of hydrogen peroxide into a corn mash located within said ethanol fermentation system, wherein a first portion of said hydrogen peroxide is added to said corn mash prior to the introduction of said peracetic acid into said fermentation mash, wherein said peracetic acid is introduced as a mixture with a second portion of said hydrogen peroxide; and
    fermenting said corn mash with an ethanol-producing yeast, at least a portion of said peracetic acid and said hydrogen peroxide being present in said corn mash during said fermenting step at levels sufficient to effect a reduction in lactic acid producing bacteria that compete with said ethanol-producing yeast for sugars contained within said corn mash; thereby reducing bacteria levels within said ethanol fermentation system;
    wherein said method is performed without the introduction of antibiotic compounds into said corn mash, and said peracetic acid is introduced into said corn mash at a level of between 5 to 30 ppm, said hydrogen peroxide compound is introduced into said fermentation mash at a total level of between 5 to 40 ppm, and wherein said corn mash comprises an aqueous suspension of fiber.

2. The method of claim 1, wherein said peracetic acid is introduced into said ethanol fermentation system in a sufficient quantity so as to prevent lactic acid levels within said system from exceeding 0.20% by weight of a liquid portion of said corn mash.

3. The method of claim 1, wherein said ethanol fermentation system further comprises a quantity of distiller's grain derived from said corn mash, wherein said method further comprises recovering said quantity of distiller's grain from said ethanol fermentation system, said distiller's grain comprising less than 1 ppm of said peracetic acid or said hydrogen peroxide.

4. The method of claim 3, wherein said distiller's grain is free of antibiotic compounds.

5. The method of claim 1, wherein said peracetic acid is provided as a mixture with a germicidal fatty acid.

6. The method of claim 1, wherein said ethanol fermentation system comprises:
    at least one fermentation mash cooler;
    a fermentation tank located downstream from said cooler; and
    at least one injection station adapted to deliver a quantity of said peracetic acid and said hydrogen peroxide into said corn mash located within said ethanol fermentation system.

7. The method of claim 6, wherein said at least one fermentation mash cooler comprises a primary mash cooler and a secondary mash cooler.

8. The method of claim 7, wherein said at least one injection station comprises a header disposed between said primary and secondary mash coolers.

9. The method of claim 6, wherein said at least one injection station is adapted to deliver said peracetic acid and said hydrogen peroxide into said fermentation tank.

10. The method of claim 6, wherein said ethanol fermentation system further comprises separation equipment operable to recover a distiller's grain product from said corn mash exiting said fermentation tank.

11. The method of claim 10, wherein said distiller's grain product comprises less than 1 ppm of said peracetic acid.

12. The method of claim 1, wherein said mixture comprises 5% to 30% by weight of said peracetic acid and 15% to 55% by weight of said hydrogen peroxide.

13. The method of claim 1, wherein said peracetic acid and said hydrogen peroxide are introduced into said corn mash prior to the introduction of yeast.

14. The method of claim 1, wherein said corn mash further comprises a member selected from the group consisting of protein, oil, and combinations thereof.

15. The method of claim 1, wherein said hydrogen peroxide is added to said corn mash at a location within said ethanol fermentation system that is upstream from a location within said ethanol fermentation system at which said peracetic acid is introduced.

16. The method of claim 1, wherein said first portion comprises from 12 ppm to 35 ppm of said hydrogen peroxide.

* * * * *